United States Patent [19]

Jefferson

[11] Patent Number: 5,688,007
[45] Date of Patent: Nov. 18, 1997

[54] CONTACT LENS INSERTER/REMOVER

[76] Inventor: Joann F. Jefferson, P.O. Box 6582, Charlottesville, Va. 22906

[21] Appl. No.: 725,289

[22] Filed: Oct. 2, 1996

[51] Int. Cl.$^6$ ................................................. A61F 9/00
[52] U.S. Cl. .................................... 294/1.2; 294/64.1
[58] Field of Search ................................ 294/1.2, 64.1; 15/341, 344, DIG. 1; 206/5.1; 269/21; 606/107

[56] References Cited

U.S. PATENT DOCUMENTS

| | | | |
|---|---|---|---|
| 3,129,971 | 4/1964 | Kobler | 294/1.2 |
| 3,139,298 | 6/1964 | Grabiel | 294/1.2 |
| 3,294,434 | 12/1966 | Sinn | 294/64.1 |
| 3,878,076 | 4/1975 | Barnett | 294/1.2 |
| 4,037,866 | 7/1977 | Price | 294/1.2 |
| 4,042,999 | 8/1977 | Triantafyllou | 294/64.1 X |
| 4,378,126 | 3/1983 | Procenko | 294/1.2 |
| 4,527,824 | 7/1985 | Rosenfeld | 294/64.1 |

Primary Examiner—Johnny D. Cherry

[57] ABSTRACT

A contact lens inserter/remover, comprising, a tubular casing having an interior chamber of a cylindrical configuration with a concave lower first end and a planar open second upper end. A fan within the chamber is adapted for rotation about an axis co-extensive with the axis of the casing and an associated motor to rotate the fan in a first direction and a second direction with an associated power source adjacent to the motor. The casing has a reduced diameter cylindrical extension at the lower first end with a plurality of apertures at the concave end for attracting or repelling a contact lens in contact therewith when the motor is energized. The casing also has air flow apertures on the side of the fan remote from the concave end. A cap is provided at the upper end of the casing with screw threads for coupling with the upper end to allow the addition or removal of the power source from the casing.

5 Claims, 4 Drawing Sheets

FIG. 1
FIG. 2
FIG. 3
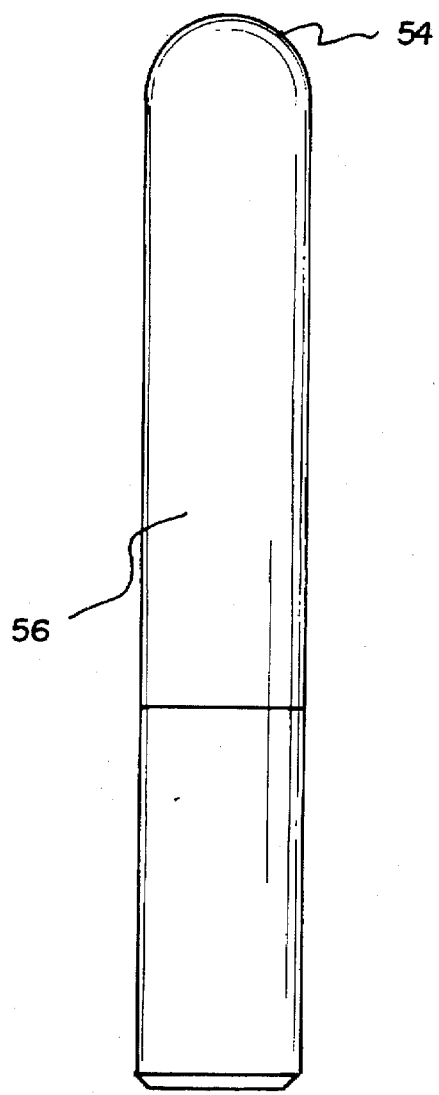
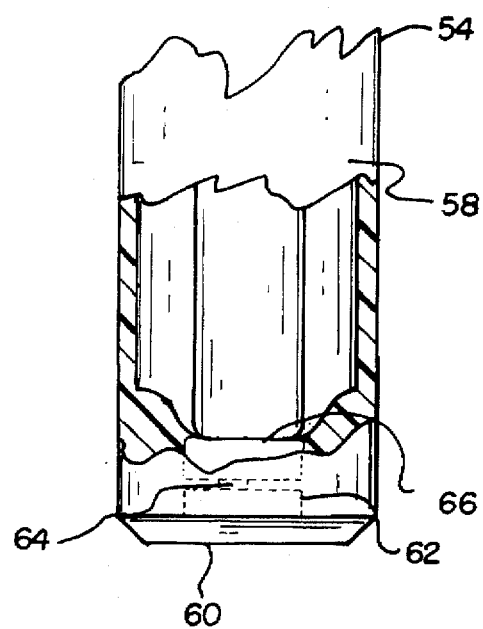
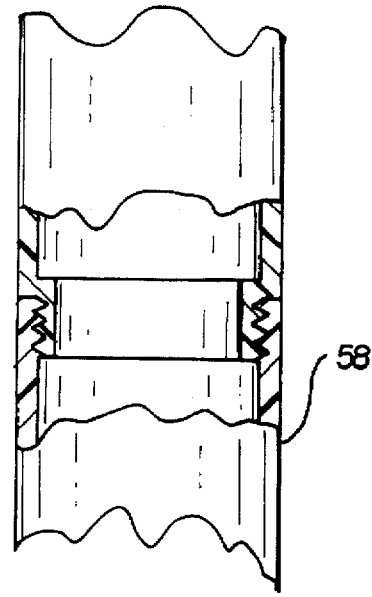

CONTACT LENS INSERTER/REMOVER

BACKGROUND OF THE INVENTION

1. Field of the Invention

The present invention relates to a contact lens inserter/remover and more particularly pertains to handle contact lenses in a more secure and sanitary manner.

2. Description of the Prior Art

The use of article handling devices of various designs and configurations is known in the prior art. More specifically, article handling devices of various designs and configurations heretofore devised and utilized for the purpose of moving objects between locations through various methods and apparatuses are known to consist basically of familiar, expected and obvious structural configurations, notwithstanding the myriad of designs encompassed by the crowded prior art which have been developed for the fulfillment of countless objectives and requirements.

By way of example, the prior art discloses in U.S. Pat. No. 5,246,259 to Hellenkamp et al. an applicator device for positioning of a contact lens on the human eye.

U.S. Pat. No. 4,201,408 to Tressel discloses a contact lens insertion and removal device.

U.S. Pat. No. 4,221,414 to Schrier discloses a contact lens insertion and removal device.

U.S. Pat. No. 4,326,742 to Ingram discloses a method and apparatus for inserting and removing soft contact lens.

U.S. Pat. No. 4,986,586 to Eilrich et al., discloses a device for removing soft contact lens.

In this respect, the contact lens inserter/remover according to the present invention substantially departs from the conventional concepts and designs of the prior art, and in so doing provides an apparatus primarily developed for the purpose of handling contact lenses in a more secure and sanitary manner.

Therefore, it can be appreciated that there exists a continuing need for new and improved contact lens inserter/remover which can be used for handling contact lenses in a more secure and sanitary manner. In this regard, the present invention substantially fulfills this need.

SUMMARY OF THE INVENTION

In view of the foregoing disadvantages inherent in the known types of article handling devices of various designs and configurations now present in the prior art, the present invention provides an improved contact lens inserter/remover. As such, the general purpose of the present invention, which will be described subsequently in greater detail, is to provide a new and improved contact lens inserter/remover apparatus and method which has all the advantages of the prior art and none of the disadvantages.

To attain this, the present invention essentially comprises a new and improved contact lens inserter/remover, comprising, in combination, a tubular casing having an interior chamber of a cylindrical configuration with a concave lower first end and a planar open second upper end. A fan within the chamber is adapted for rotation about an axis co-extensive with the axis of the casing and an associated motor to rotate the fan in a first direction for drawing a vacuum at the first end of the casing and a second direction for effecting a blowing discharge of air at the first end of the casing with an associated power source adjacent to the motor. The casing has a reduced diameter cylindrical extension at the lower first end with a plurality of apertures at the concave end for attracting or repelling a contact lens in contact therewith when the motor is energized. The casing also has air flow apertures on the side of the fan remote from the concave end. A cap at the upper end of the casing with screw threads is for coupling with the upper end to allow the addition or removal of the power source from the casing. A housing for supporting the casing is formed of a top hollow cylindrical portion with an open bottom end and a bottom hollow cylindrical portion with an open top end. The top hollow portion and the bottom hollow portion are adapted to be screwably coupled together at the open ends thereof for containing the casing therein. The bottom hollow portion further includes a battery. The battery is coupled through electrical lines to a thermal resistant element which functions as the heating component and, a sterilizing agent for the concave end of the casing. Thus, when the battery is energized and the sterilizing agent heated as a result of such electrical power, it will function to sterilize the concave end of the housing when ever brought in contact therewith for greater sanitation to the system.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved contact lens inserter/remover which has all the advantages of the prior art article handling devices of various designs and configurations and none of the disadvantages.

It is another object of the present invention to provide a new and improved contact lens inserter/remover which may be easily and efficiently manufactured and marketed.

It is a further object of the present invention to provide a new and improved contact lens inserter/remover which is of a durable and reliable construction.

An even further object of the present invention is to provide a new and improved contact lens inserter/remover which is susceptible of a low cost of manufacture with regard to both materials and labor, and which accordingly is then susceptible of low prices of sale to the consuming public, thereby making such article handling devices of various designs and configurations economically available to the buying public.

Still yet another object of the present invention is to provide a new and improved contact lens inserter/remover which provides in the apparatuses and methods of the prior art some of the advantages thereof, while simultaneously overcoming some of the disadvantages normally associated therewith.

Still another object of the present invention is to handle contact lenses in a more secure and sanitary manner.

Lastly, it is an object of the present invention to provide a new and improved contact lens inserter/remover, comprising, a tubular casing having an interior chamber of a cylindrical configuration with a concave lower first end and a planar open second upper end. A fan within the chamber is adapted for rotation about an axis co-extensive with the axis of the casing and an associated motor to rotate the fan in a first direction and a second direction with an associated power source adjacent to the motor. The casing has a reduced diameter cylindrical extension at the lower first end with a plurality of apertures at the concave end for attracting or repelling a contact lens in contact therewith when the motor is energized. The casing also has air flow apertures on the side of the fan remote from the concave end. A cap is provided at the upper end of the casing with screw threads for coupling with the upper end to allow the addition or removal of the power source from the casing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of the preferred embodiment of the present invention depicting the housing thereof.

FIG. 2 is a cross sectional view of the housing shown in FIG. 1 for containing the casing of the present invention.

FIG. 3 is yet another cross sectional view of the housing of FIG. 1 showing the coupling of the top and bottom portions thereof.

Similar reference characters refer to similar parts throughout the several views of the drawings.

DESCRIPTION OF THE PREFERRED EMBODIMENT

Figure 4:
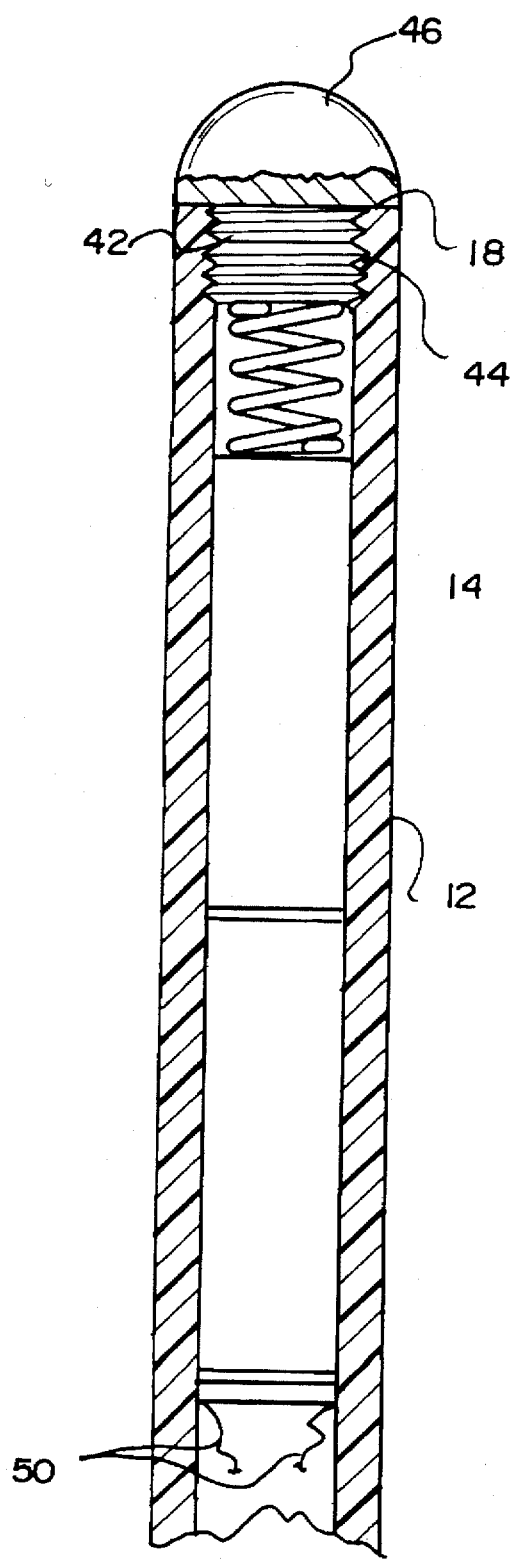
FIG. 4 is a cross sectional view taken at the upper extent of the casing.
Figure 5:
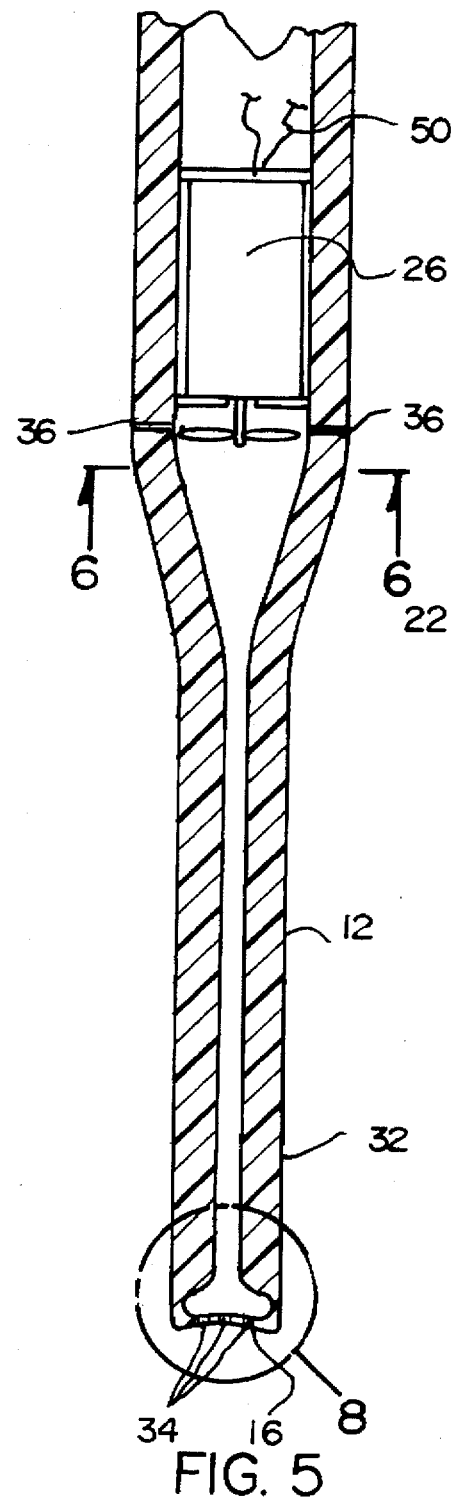
FIG. 5 is a cross sectional view taken at the lower extent of the casing.
Figure 6:
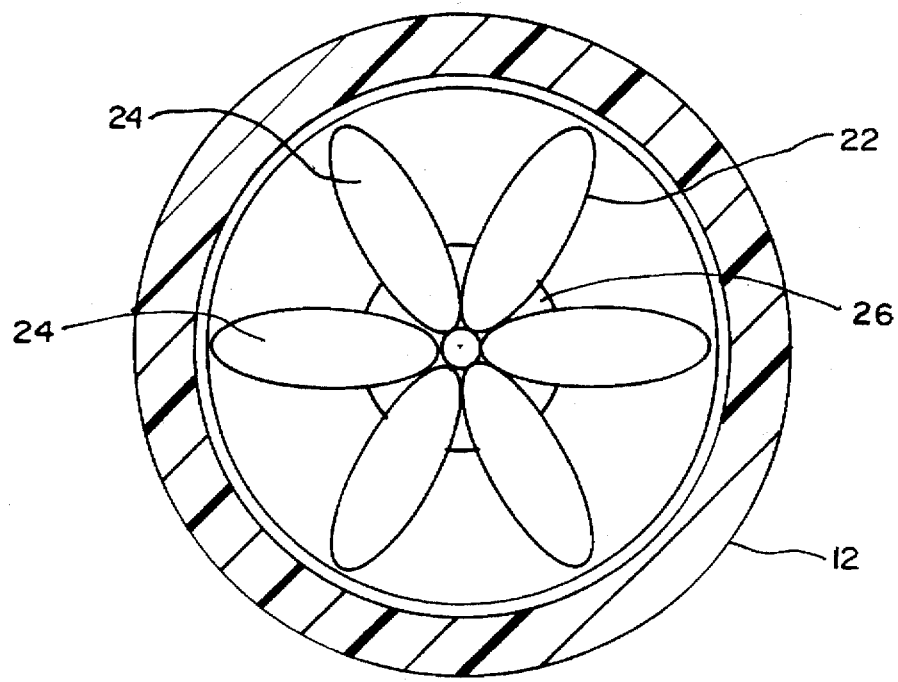
FIG. 6 is a cross sectional view taken along line 6—6 of FIG. 5.
Figure 7:
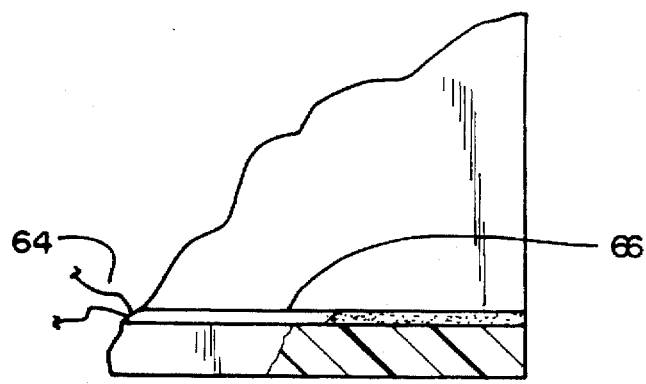
FIG. 7 is an enlarged front elevational view partly in section.
Figure 8:
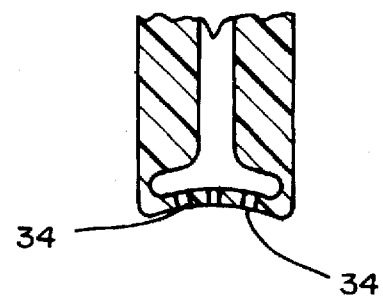
FIG. 8 is an enlarged showing taken at circle 8 of FIG. 5.
Figure 9:
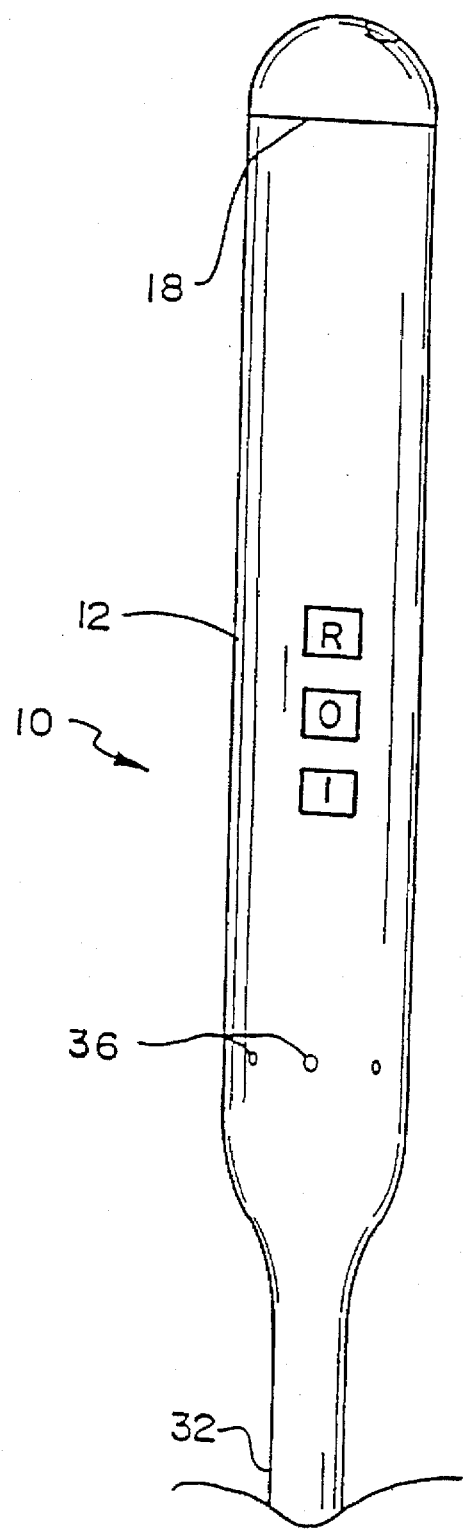
FIG. 9 is a side elevational view of the exterior of the casing of the present invention.

With reference now to the drawings, and in particular to FIG. 1 thereof, a new and improved contact lens inserter/remover embodying the principles and concepts of the present invention and generally designated by the reference numeral 10 will be described.

The present invention, the new and improved contact lens inserter/remover, is comprised of a plurality of components. Such components in their broadest context include a tubular casing, a fan, a casing, a cap, a switch, and a housing. Such components are individually configured and correlated with respect to each other so as to attain the desired objective.

More specifically, the present invention is a system 10 which has as its central component a tubular casing 12. The tubular casing has an interior chamber 14. Such chamber is of a cylindrical configuration. The casing has a concave lower first end 16 and a planar open second end 18.

Located in a central extent of the chamber of the casing is a fan 22. The fan has a plurality of blades 24 adapted for rotation about an axis which is coextensive with the axis of the casing. In association with the fan is an associated motor 26. The motor functions to rotate the fan in a first direction or a second direction. When rotated in a first direction, the fan will function to draw a vacuum at the first end of the casing for the purpose of holding a contact lens. When rotated in the second direction, the fan will effect a blowing discharge of air at the first end of the casing. In association with the fan, blades and motor is an associated power source operatively coupled with respect to the motor for powering purposes.

The casing is configured to have a reduced diameter cylindrical extension 32 at its lower first end. At the end of such extension are a plurality of apertures 34. These are located at the concave end. The apertures function in association with the fan for attracting or repelling contact lens in contact therewith whenever the motor is energized. In association with such flow of air, the casing is formed to have a plurality of air flow apertures 36 extending through the casing. Such air flow apertures are on the side of the fan remote from the concave end with its apertures.

The next component of the system is a cap 46. Such cap is located at the upper end of the casing. It is formed with screw threads 42 for coupling with screw threads 44 at the upper end of the casing. The function of the cap is to allow access to the chamber for the addition or removal of batteries from the casing.

A switch 48 is adapted to inactivate the motor or to drive the motor in a first direction and a second direction at the discretion of the user. The coupling between the switch and the motor and power source are through electrical lines 50 in a conventional manner.

Adapted to be used in association with the casing and its associated components is a housing 54. Such housing is for supporting the casing, preferably in a vertical manner. Preferably, the housing is approximately 5¼ inches in length and ¾ of an inch wide. The housing is formed of a top hollow cylindrical portion 56 with an open bottom end and a bottom hollow cylindrical portion 58 with an open top end. The top hollow portion and the bottom hollow portion are adapted to be screwably coupled together at the open ends thereof for containing the casing therein. For stability purposes, a pad 60 is fixed on the bottom hollow portion. The bottom hollow portion further includes a battery 62. The battery is coupled through electrical lines 64 to a thermal resistant element 66 which functions as the heating component and, a sterilizing agent for the concave end of the casing. Thus, when the battery is energized and the sterilizing agent heated as a result of such electrical power, it will function to sterilize the concave end of the casing when ever brought in contact therewith for greater sanitation to the system. Any one of numerous methods of controlling the power supply to the resistant element may be employed such as the employment of a computer chip or push button. It should further be noted that the material from which the housing is constructed is heat resistant.

A suctioning and blowing device that aids in inserting and removing contact lenses. It consists of a small plastic casing, electrical circuitry, batteries, fans, fastening hardware, and a plastic stand in which it is stored. It is operated off of ordinary household current or batteries. The cylindrical casing has a closed top and a funnel-shaped bottom with a small orifice. A three position switch is situated on one side of the casing just below its middle, with three settings, REMOVE, INSERT and OFF. Electrical circuitry, a miniature fan, batteries, and other necessary hardware are installed inside the casing.

To insert a contact lens, grasp the sterilized housing, place its tip over the lens in the case, move the switch to the REMOVE position and lift the lens out of the case. Place it over the cornea and move the switch to the INSERT position. To remove the lens, grasp the device, place its tip over the lens, move the switch to the REMOVE position and lift it out.

The unit is practical, efficient and easy to use. For anyone who wears contact lenses, this is an ideal product.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A contact lens inserter/remover, comprising, in combination:

a tubular casing having an interior chamber of a cylindrical configuration with a concave lower first end and a planar open second upper end;

a fan within the chamber adapted for rotation about an axis co-extensive with the axis of the casing and an associated motor to rotate the fan in a first direction for drawing a vacuum at the first end of the casing and a second direction for effecting a blowing discharge of air at the first end of the casing with an associated power source adjacent to the motor;

the casing having a reduced diameter cylindrical extension at the lower first end with a plurality of apertures at the concave end for attracting or repelling a contact lens in contact therewith when the motor is energized, the casing also having air flow apertures on the side of the fan remote from the concave end;

a cap at the upper end of the casing with screw threads for coupling with the upper end to allow the addition or removal of the power source from the casing;

a switch adapted to inactivate the motor or to drive the motor in a first direction and a second direction at the discretion of the user; and a housing formed of a top hollow cylindrical portion with an open bottom end and a bottom hollow cylindrical portion with an open top end, wherein the top hollow portion and the bottom hollow portion are adapted to be screwably coupled together at the open ends thereof for containing the casing therein, the bottom hollow portion further including a battery and a sterilizing agent at a bottom end thereof for heating the concave end of the casing when brought in contact therewith.

2. A contact lens inserter/remover, comprising:

a tubular casing having an interior chamber of a cylindrical configuration with a concave lower first end and a planar open second upper end;

a fan within the chamber adapted for rotation about an axis co-extensive with the axis of the casing and an associated motor to rotate the fan in a first direction and a second direction with an associated power source adjacent to the motor;

the casing having a reduced diameter cylindrical extension at the lower first end with a plurality of apertures at the concave end for attracting or repelling a contact lens in contact therewith when the motor is energized, the casing also having air flow apertures on the side of the fan remote from the concave end; and a cap at the upper end of the casing with screw threads for coupling with the upper end to allow the addition or removal of the power source from the casing.

3. The apparatus as set forth in claim 2 and further including a switch adapted to inactivate the motor or to drive the motor in a first direction and a second direction at the discretion of the user.

4. The apparatus as set forth in claim 2 and further including a housing formed of a top hollow cylindrical portion with an open bottom end and a bottom hollow cylindrical portion with an open top end, wherein the top hollow portion and the bottom hollow portion are adapted to be screwably coupled together at the open ends thereof for containing the casing therein.

5. The apparatus as set forth in claim 4 wherein the bottom hollow portion further includes a battery and a sterilizing agent for heating the concave end of the casing when brought in contact therewith.

* * * * *